US005795738A

United States Patent [19]
Grandi et al.

[11] Patent Number: 5,795,738
[45] Date of Patent: Aug. 18, 1998

[54] ENGINEERED PEPTIDE SYNTHETASES AND THEIR USE FOR THE NON-RIBOSOMAL PRODUCTION OF PEPTIDES

[75] Inventors: Guido Grandi, Milan; Francesca de Ferra, Lodi; Francesco Rodriguez, S. Donato Milanese, all of Italy

[73] Assignee: Eniricerche S.p.A., Milan, Italy

[21] Appl. No.: 670,901

[22] Filed: Jun. 26, 1996

[30] Foreign Application Priority Data

Aug. 9, 1995 [IT] Italy ................... MI95A1764

[51] Int. Cl.$^6$ .................. C12P 21/06; C12P 21/04; C12N 1/20; C07H 21/04
[52] U.S. Cl. ............... 435/69.1; 435/69.7; 435/252.3; 435/320.1; 536/23.2; 536/23.4
[58] Field of Search .................. 435/69.1, 69.7, 435/252.3, 320.1; 536/23.2

[56] References Cited

PUBLICATIONS

Stachelhaus et al. (Jul. 7, 1995) Rational Design of Peptide Antibiotics by Targeted Replacement of Bacterial and Fungal Domains. Science 269:69–72.

van Liempt et al. (Sep. 1991) Principles of the Molecular Construction of Multienzyme Templates for Peptide Biosynthesis in Integrated Reaction Sequences. Biomed. Biochim. Acta 50 (10/11): S256–S259.

Wiseman, A. (Feb. 1993) Designer Enzyme and Cell Applications in Industry and in Environmental Monitoring. J. Chem. Tech. Biotechnol. 56: 3–13.

Primary Examiner—Robert A. Wax
Assistant Examiner—Einar Stole
Attorney, Agent, or Firm—Oblon, Spivak, McClelland, Maier & Neustadt, P.C.

[57] ABSTRACT

The present invention relates to the construction of functional engineered peptide synthetases capable of displaying a correct activity and their use for the non-ribosomal production of modified peptides.

13 Claims, 4 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Gly  Gly  Xaa  Ser  Xaa
    1                        5

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

GCATATGTGA ATTCGGATTC AGCGCTTCCT GGG                                          33

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:3:

TTCCTTATGA GCTCCTCTTG AATTTTCGCC GTCA                                         34

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

AACAAAGAGC TCGGGATTGA TCCTTCCA                                                          28

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear

```
( i i ) MOLECULE TYPE: other nucleic acid ( x i ) SEQUENCE DESCRIPTION: SEQ ID NO:5:

GTGTGGATCC    ATTTGAAACC    GTTACGGTTT    G                                    3 1
```

ENGINEERED PEPTIDE SYNTHETASES AND THEIR USE FOR THE NON-RIBOSOMAL PRODUCTION OF PEPTIDES

BACKGROUND OF THE INVENTION

1. Field of the Invention

The present invention relates to the construction of functional engineered peptide synthetases capable of displaying a correct activity and their use for the non-ribosomal preparation of modified peptides.

2. Description of the Related Art

The term "modified peptides" refers to analogs of native peptides (wild type) or peptides having a new amino acid sequence.

Peptide synthetases are enzymatic complexes of eucaryotic or procaryotic origin, which are responsible for the synthesis of peptides by a non-ribosomal mechanism, also known as thiotemplate synthesis (Kleinkauf, H. and von Doehren, H.(1987) Ann. Rev. Microbiol., 41:259–289).

Such peptides, which can be up to 20 or more amino acids in length, can have a linear, cyclic (cyclosporine, tyrocidine, mycobacilline, surfactin and others) or branched cyclic structure (polymyxin, bacitracin and others) and often contain amino acids not present in proteins or modified amino acids through methylation or epimerization.

Peptide synthetases are described as multienzymatic complexes consisting of one or more polypeptides (enzymatic subunits). The characteristic of these complexes is the presence on the same polypeptide of one or more repeated structural units (super-domains) inside of which there is a region, called activation domain (DDA), used for recognizing a specific amino acid.

Each DDA catalyzes a series of enzymatic reactions which at the end lead to the inclusion of each amino acid in the peptide chain and which comprise:

1-recognition of the amino acid;
2-activation of the amino acid as aminoacyladenylate;
3-binding of the activated amino acid to the enzyme by the thioester bond between the carboxylic group of the amino acid and the SH group of an enzymatic co-factor (5-phosphopantetheine) which is itself bound to the enzyme inside each DDA; and finally
4-formation of peptide bonds among the amino acids.

The DDAs can be beside at the carboxylic end with regions associated with the methylation or racemization of the amino acids from configuration L to D.

Finally, the peptide release and ending functions are also associated with the multienzymatic complex which, probably, are located in a conserved domain at the end of the last DDA.

In peptide synthetases there are as many DDAs as the amino acids which form the peptide. For example, the complex of surfactin synthetase which catalyzes the polymerization of the lipopeptide having the following structure:

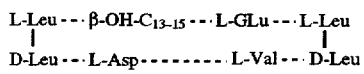

consists of three polypeptides of which the first two include three DDAs each, whereas the third has only one DDA. These domains are responsible for the recognition, activation, binding and polymerization of L-Glu, L-Leu, D-Leu, L-Val, L-Asp, D-Leu and L-Leu amino acids.

To this enzymatic organization corresponds, on the genes of the synthetases, a similar organization in discreet and repeated units (modules) which encode the super-domains.

This modular structure is conserved among the bacterial and fungal peptide synthetases, as shown by the sequence characterization data of the srfA operon (Cosmina et al. Mol. Microbiol., 8: 821–831, 1991), as well as grsA and grsB operons (Kratzschmar ae al., J. Bacteriol., 171: 5422–5429, 1989), tycA and tycB (Weckrmann et al., Nucl. Acid. Res.. 16: 11841–11843) and ACV from various fungal species (Smith et al. EMBO J., 9:741–747, 1990).

Inside the activation domains, even of distant species, there are sequences with high homology, some of which are conserved and specific for all peptide synthetases.

Therefore, a characteristic of the thiotemplate synthesis is that the sequence of the peptide product is determined, at the level of genes and therefore at the enzyme level, by the order and the sequence characteristics of the single activation domain.

Many of the peptides synthesized by the non-ribosomal method have proven antibiotic, antifungine, immunosuppressive and surfactant properties.

The preparation of molecules with improved properties with respect to the known ones (for example molecules having an immunosuppressive activity similar to that of Cyclosporin A, but with less toxicity) or with new activities can have a considerable commercial importance.

At the present the available techniques for the preparation of these molecules include:

1) selection of new producer microorganisms;
2) preparation of mutants by mutagenesis of wild type stains with chemical agents;
3) modification of amino acid substrates for the growth of the peptide-producing organisms in the attempt to include different amino acids in the peptides.
4) chemical synthesis.

These methods are usually very expensive in terms of time, present a high level of uncertainty as to the probability of obtaining new molecules, offer very few possibilities of directing the modification of the peptide towards suitably designed structures and, in case of chemical synthesis, the production on a large scale of complex molecules is particularly onerous and difficult.

Presently, therefore, there is the need for a method which could allow the efficient production of modified or new peptides without the above-said disadvantages.

SUMMARY OF THE INVENTION

It has been now found that it is possible to satisfy these needs by the process of the present invention, which uses functional engineered peptide synthetases which are capable of displaying a correct activity.

In particular, according to the present invention, it has been found that a necessary and sufficient condition, in order to produce and secrete a peptide with high quantities, is that the last activation domain of a peptide synthetase properly designed, has its C-terminal end fused to the sequence present on the C-terminal end of the last activation domain of a peptide synthetase.

In other words, disposing of the genes which code for the a, b, c, d domains capable of recognizing A, B, C, and D amino acids, it is possible to build an engineered peptide synthetase a-b-c-d which produces the A-B-C-D peptide which is secreted correctly, if the end of the D domain is fused to the sequence present at the C-terminal end of the last activation domain of a peptide synthetase.

According to this, the present invention regards a method for the non-ribosomal production of modified peptides, which comprises:

(a) isolating from chromosomal DNA of strains producing peptide synthetases the sequences which code predetermined activation domains of amino acids and fusion of these sequences in a predetermined order established by the order of the amino acids in the desired peptide;

(b) fusion of the 3-terminal nucleotide sequence downstream of the last activation domain of a peptide synthetase in the region at the end of the sequence which encodes the conserved site Gly-Gly-(His-Asp)-Ser-(Ile-Leu)(SEQ ID NO:1) of the thioester bond of the last activation domain of the peptide synthetase engineered as reported in step (a);

(c) introducing the gene construction obtained in (b) in a vector under the control of suitable transcription and translation signals;

(d) transforming a microorganism with the vector obtained in (c);

(e) cultivating under suitable conditions the microorganism transformed as in (c); and finally (f) isolating the peptide from the culture medium.

It is another object of the present invention to provide a method for the preparation of engineered peptide synthetases and peptide synthetases thus obtained.

Further objects of the present invention will appear from the reading of the description and from the example which follows.

BRIEF DESCRIPTION OF THE DRAWINGS

In order to provide a better definition of the present invention a reference is made to the following figures.

DESCRIPTION OF THE PREFERRED EMBODIMENTS

Figure 1:
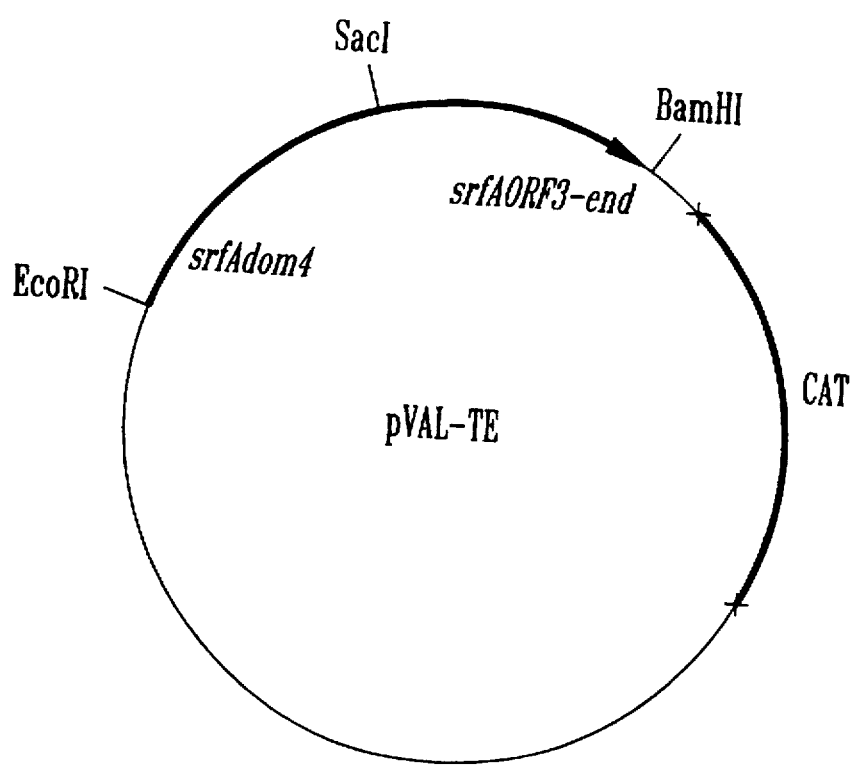
FIG. 1 shows the restriction map of the pVAL-TE plasmid.

In step (a) of the method of the present invention the isolation and fusion of the activation domains, also from peptide synthetases of organisms phylogenetically separated, can be carried out by, for example, the techniques described in the Italian patent application MI93001534.

In step (b) of the method of the present invention, the fusion of the 3-terminal nucleotide sequence is carried out, preferably, in the region of at least 10 amino acid residues downstream of said conserved site.

In case that the last activation domain of the synthetase engineered according to the method of the present invention codes for an amino acid in configuration D or for a methylated amino acid, the region downstream of the conserved site will contain the domain, or part of it, which codes the methylation or epimerization function.

Examples of vectors suitable for the purposes of the present invention can be selected from expression or integration plasmids. The latter are plasmids which are not capable of being autonomously replicated in the host microorganism, but which can be integrated in its chromosome by means of a Campbell recombination (Vosman, B. et al. (1986), Mol. Gen. Genet., 204: 524–531). The recombination occurs among sequences of homologous DNA present on the plasmid and on the chromosome. To aid the screening procedure and isolate recombinants, the plasmid must contain a marker selectable in the host strain. Integration plasmids can be selected for example from pJM103 and pJM102 containing the CAT gene (chloramphenicol acetyltransferase) as a marker which gives resistance to the chloramphenicol antibiotic.

Examples of microorganisms which can be used in the method of the present invention are selected from bacteria, yeasts or fungi which produce a peptide synthetase.

The transformation of said organisms and their selection are generally carried out with the conventional techniques (Maniatis, et al.—Molecular cloning—A Laboratory Manual—Cold Spring Harbor Laboratory ed., New York).

The microorganisms thus isolated can be cultivated under suitable conditions and the produced peptides are conveniently recovered and purified by usual techniques.

As an alternative, the peptide synthetases expressed by these microorganisms can be isolated, purified and used for the synthesis in vitro of the peptides of interest. The peptide synthetases can be used as such or immobilized on insoluble solid supports to allow their continual use.

In order to provide an example, without however limiting the present invention, the construction of engineered peptide synthetases is reported, starting from the srfA operon which encodes surfactin synthetase.

The 3-terminal region of srfAORF3 which follows the sequence encoding the conserved site Gly-Gly-(Hisp/Asp)-Ser-(Ile/Leu)(SEQ ID NO:1) of the thioester bond of the last amino acid binding domain of surfactin synthetase is homologous to the 3-terminal regions of the last activation domains of other peptide synthetases. This region, and in particular the 260 amino acids long fragment following the SacI site (hereby denominated TE region) was fused to the fourth activation domain of surfactin synthetase to test the possibility of using this region for the creation of hybrid peptide synthetases.

The fusion construct was inserted in the chromosome of B. subtilis by use of the integrative plasmid (pVAL-TE) as described in example 1. The map of this plasmid is depicted in FIG. 1.

The transformation of surfactin producing B. subtilis strain JH642 with the integrative pVAL-TE plasmid, can result in the insertion of the plasmid in two possible regions of srfA depending on the point where Campbell recombination ensues (see FIG. 2):

the recombination in the fourth amino acid activating domain generates hybrid synthetase formed by 4 complete activation domains the last of which is fused to the TE region.

the recombination at the level of the SrfA TE region does not imply any modification of the wild type surfactin synthetase.

In order to demonstrate that the presence of the TE region fused to the SrfA domain 4 is a fundamental condition to obtain a high production of the tetrapeptide, the JH642 strain was transformed with a plasmid whose integration in SrfA could occur after domain 4 without leading to the fusion of the TE region after domain 4 itself.

In particular, plasmid pSM537 was used, which, after transformation in *B.Subtilis* JH642, produced a mutant strain (*B. subtilis* SMS347) in which the complete srfAORF3 and the part of srfAORF2 which includes a portion of the domain 5 and the complete domain 6 of the surfactin synthetase operon were deleted.

Results reported in example 1 show that:
1. the fusion of the last 260 amino acids of the subunit srfAORF3 downstream the fourth activation domain of surfactin synthetase results in the formation of an active peptide synthetase which synthesizes the lipotetrapeptide having the sequence Fatty Acid-Glu-Leu-DLeu-Val. This lipopeptide is secreted in quantities comparable to the native surfactin synthetase product.
2. the absence of this fusion leads to the synthesis of a non-functional peptide synthetase.

In conclusion, the method of the present invention enables:

the production in great quantities of new peptides with modified sequence as compared to the natural products of peptide synthetases;

the possibility to synthesize peptides containing a variety of non natural and/or modified amino acids (present in peptides synthesized by means of non-ribosomal process) and which can be used for the synthesis of analogs of peptides.

The following example has the purpose of further illustrating the present invention without limiting it.

EXAMPLE 1

The present example discloses the construction of a *B. subtilis* strain expressing a peptide synthetase formed by the first four domains of surfactin synthetase and wherein the fourth domain is fused to the 260 amino acid long C-terminal region of the third subunit of surfactin synthetase (srfAORF3). The isolation and the characterization by amino acid analysis of the peptides produced are also described.

This strain was constructed by inserting in the chromosome the integrative pVAL-TE plasmid, whose map is illustrated in FIG. 1, using a Campbell recombination event.

A) Construction of pVAL plasmid p-VAL plasmid was obtained by cloning in *E.coli* the gene amplification product obtained using the following oligonucleotides (primers)(SEQ ID NO:2,3)

1) 5´-GCATATGTGAATTCGGATTCAGCGCTTCC-TGGG-3

2) 5-TTCCTTATGAGCTCCTCTTGAATTTTCGCC-GTCA-3 each containing the recognition sites of restriction enzymes EcoRI and SacI respectively in vector pJM103. (M. Perego and J. Hoch (1991), J. Bacteriol., 173: 2514–2520). The DNA fragment amplified with these primers from chromosomal DNA of *B. subtilis* JH642 srf+ (surfactin producer) corresponds to the region of the fourth activating domain of operon srfA which encodes the portion of srfAORF2 included between residues 545 and 1011. The fragment, digested with EcoRI and SacI enzymes was cloned between sites EcoRI and SacI of pJM103 (which contains the genes which confer resistance to ampicillin and chloramphenicol) and Ampicillin resistant clones were selected. Plasmid DNA (pVAL) from one of the Ampicillin-selected clones was used to transform cells of *B. subtilis* made competent as described by Perego and Hoch (M. Perego and J. Hoch (1991), J. Bacteriol., 173: 2514–2520). The transformants, in which the plasmid was integrated in the chromosome by single crossing-over Campbell type recombination, were selected on the sporulation Shaeffer medium (Spo) added with 5 µg/ml of chloramphenicol.

pVAL-TE plasmid was obtained by cloning between sites SacI and BamHI of pVAL the gene amplification product obtained using the following oligonucleotides as primers (SEQ ID NO:45):

3) 5-AACAAAGAGCTCGGGATTGATCCTTCCA-3
and 4) 5-GTGTGGATCCATTTGAAACCGTT-ACGGTTTG-3 and the chromosomal DNA of JH642 as template, according to known procedures.

The amplified region of 800 pairs of bases, comprised between the SacI and BamHI restriction sites, encodes the C-terminal portion of srfAORF3 included between amino acids 1016 and 1275. The gene amplification product was then digested with SacI and BamHI and cloned in pVAL digested with the same enzymes using standard procedures.

The resulting plasmid, pVAL-TE was used to transform competent cells of JH642 and the transformants were selected on Spo plates containing chloramphenicol (5 µg/ml).

Figure 2A:
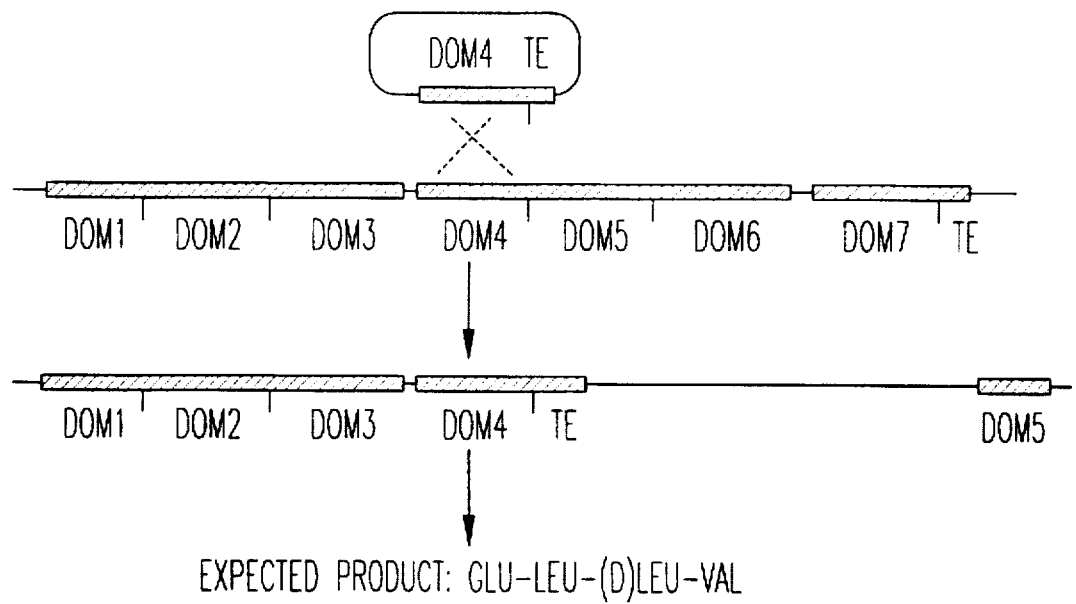
FIG. 2 shows the possible Campbell integration which can occur within the SrfA operon after transformation of strain JH642 with pVAL-TE plasmid.
Figure 2B:
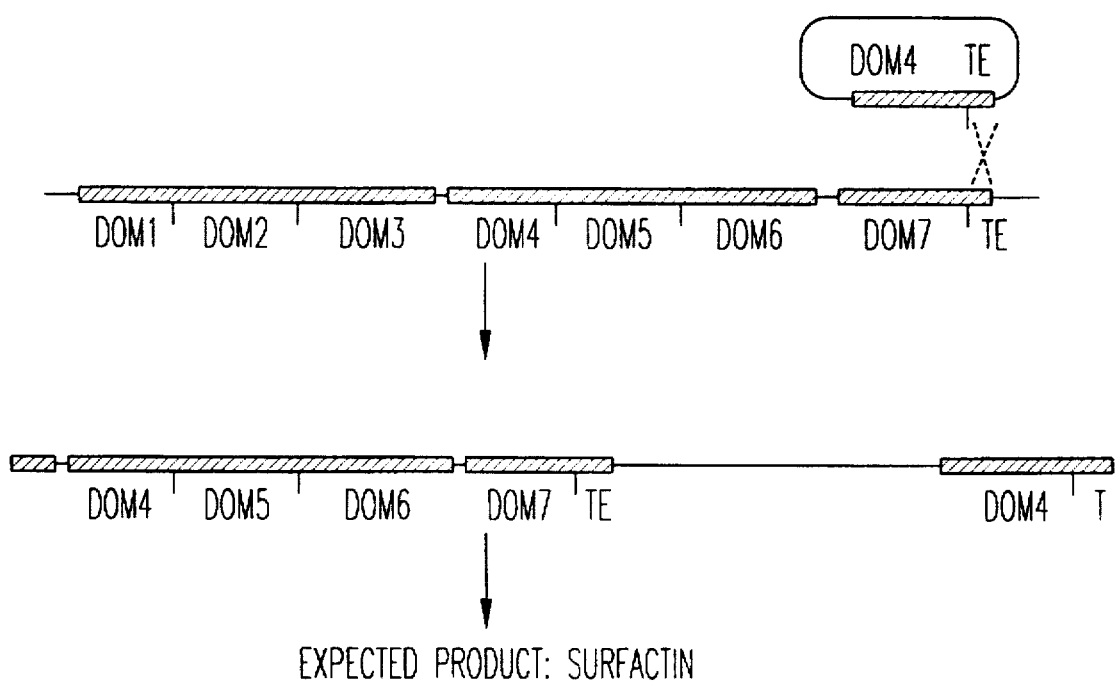

The possible gene configurations of surfactin synthetase obtainable by transformation of *B. subtilis* with pVAL-TE plasmid are shown in FIG. 2.

Out of the integration of pVAL-TE two classes of transformants can be derived. In the first class (A in FIG. 2), the recombinant event has occurred upstream of the SacI site of the insert, so that the resulting surfactin synthetase consists of srfAORF1 and a hybrid protein constituted by the first activation domain of srfAORF2 fused to the last 260 amino acids of srfAORF3.

In the second class (B in FIG. 2), the recombination has occurred in the region downstream of the SacI site and results in the formation of a wild type surfactin synthetase in which srfAORF1, srfAORF2 and srfAORF3 are complete. Peptides produced by representative strains of these two classes were analyzed by HPLC, TLC and aminoacid analysis.

B) Construction of *B. subtilis* SMS347

The *B. subtilis* SMS347 strain was obtained by transforming *B. subtilis* JH642srf with plasmid pSM537 linearized with restriction enzyme BclI. Said plasmid was obtained by transforming *E. coli* with a ligase mixture containing plasmid DNA pJM103 linearized with PstI, the fragment BclI-NsiI corresponding to the sequence of gene srfAORF2 from residue 13442 to residue 14324 and fragment NisiI-BclI corresponding to the sequence of gene srfAORF2 from residue 17453 to residue 21074. The transformants were selected on plates of sporulation media containing 5 mg/ml of chloramphenicol. Thirty-six colonies (CmR) were inoculated in LB culture medium and chromosomal DNA was extracted from the cultures. After the integration by double crossing-over, the chromosomal fragment from residue 14324 to residue 17453 of SMS347 was substituted with the region of 3700 bp of pJM103 containing the chloramphenicol resistance gene.

C) Production of peptides

The growth conditions used to obtain the production of peptides are the same which were used for the synthesis of surfactin.

The colonies were cultured for 16 hours in rich culture medium (VY=veal Infusion Broth 25 g/l, Yeast Extract 5 g/l) at 37° C., then the culture was diluted 1:20 in minimum culture medium having the following composition:

$NH_4Cl$ 4.00 g
$KH_2PO_4$ 4.00 g
$Na_2HPO_4$ 5.64 g
glucose 4%
phenylalanine 50 mg/l
tryptophane 50 mg/l
stock of salts 100×1 ml
The salts stock is constituted by:
$MgSO_4.7H_2O$ 20.00 g
$CaCl_2$ 0.10 g
$FeSO_4.7H_2O$ 2.00 g
EDTA 0.15 g
$MnCl_2.6H_2O$ 30 mg
$H_2O$ 1 liter
pH<2

After 5–7 hours of growth at 37° C. with stirring, the cells were pelleted by centrifugation and the medium was acidified at pH 2 to precipitate the peptides.

Figure 3A:
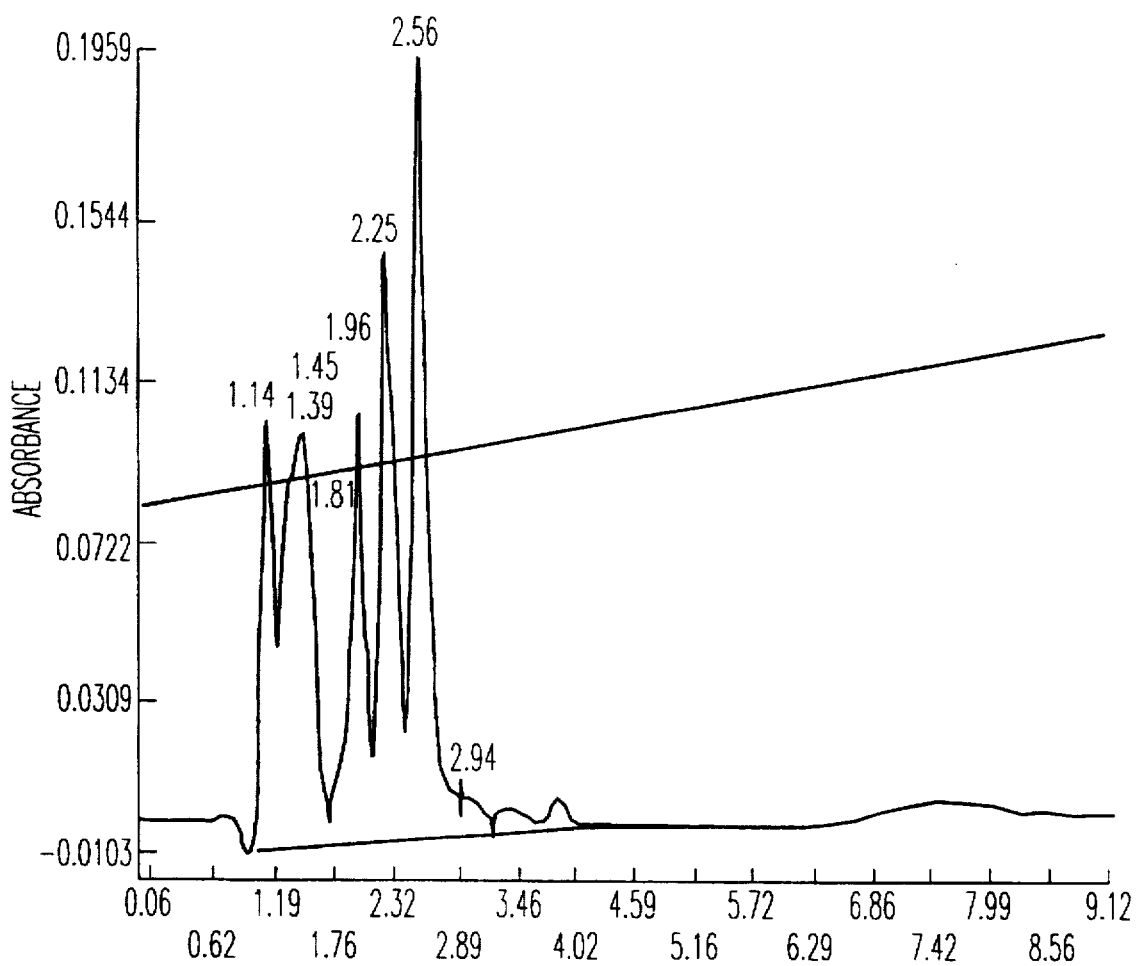
FIG. 3 shows chromatograms of peptides purified from the culture supernatants of strains transformed with pVAL-TE. In particular, in A) the peptide deriving from the strain in which pVAL-TE is integrated in activation domain 4 of SrfA is shown, while in B) the peptide purified from the culture medium of the recombinant strain having pVAL-TE integrated at the 3 terminal of the seventh activation domain of SrfA is shown.
Figure 3B:
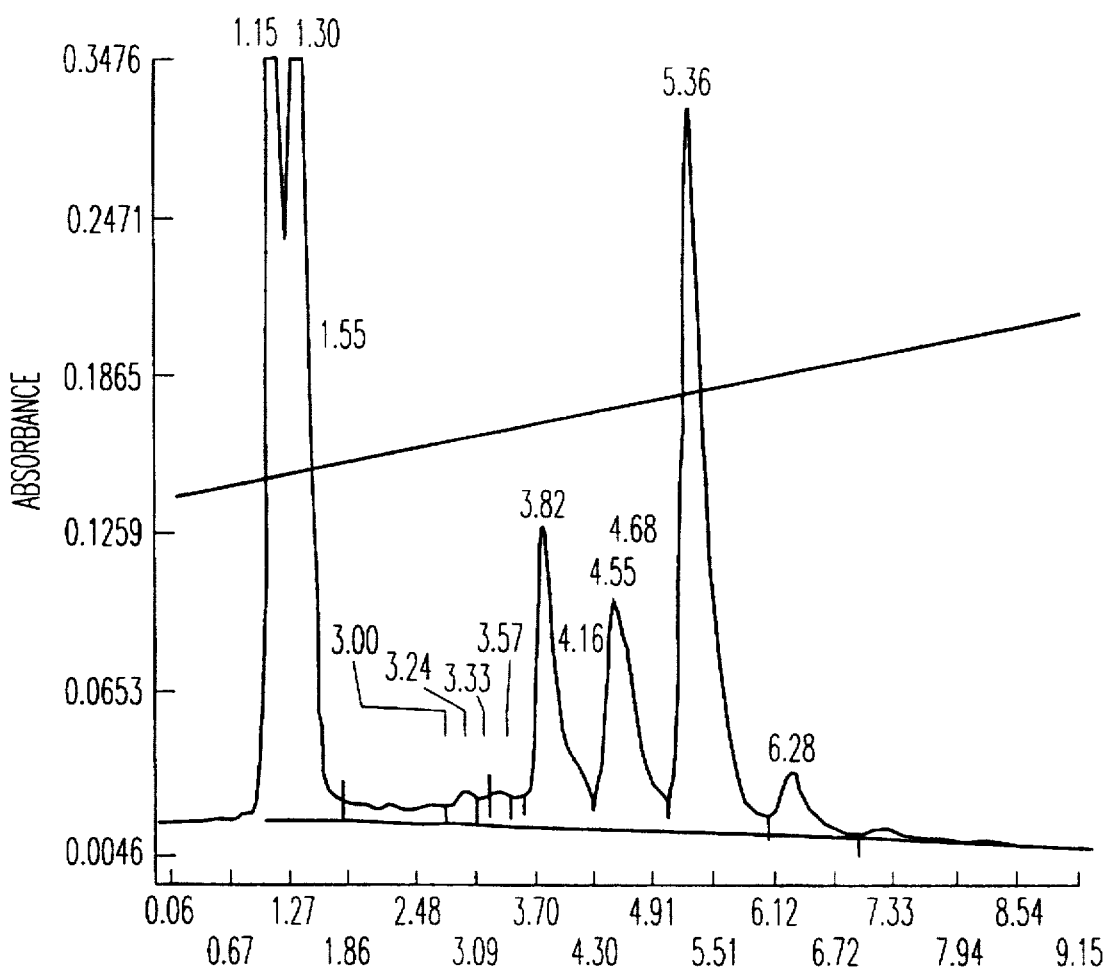

The precipitate was dried and re-suspended in methanol concentrating it 10 times the volume of the starting culture. HPLC Analysis For the HPLC analysis, 20 ml of such concentrate were injected in a C8 column (LiCrospher® RP-Select B 5 mm 125×4 mm) to which a gradient was applied ranging from 70 to 95% acetonitrile in water (both solvents containing TFA 0.05%) in 10 minutes, followed by 5 minutes at 95%, at 1 ml/min flow rate. The elution was monitored at 220 nm of absorbance. The results are shown in FIG. 3.

While strain SMS347 does not produce appreciable quantities of peptide, the strain in which the activation domain of valine is fused to the carboxyl terminal region of srfA3 (JH642(pVAL-TE)A) secretes an appreciable quantity of material which absorbs at $A_{220}$.

The strain in which pVAL-TE is integrated in order to produce srfAORF1, srfAORF2 and srfAORF3 wild type (JH643(pVAL-TE)B) produces normal quantities of lipopeptide which co-elutes with the standard of surfactin.

5 ml of the material extracted from the culture medium of these two strains were analyzed by TLC on silica gel plates (Merck Silicagel® 60, 0.25 mm) using a mixture of acetone/butanol/$H_2O$ 5:3:1 as the mobile phase. The peptides are detected by spraying the plate with water.

For the amino acid analysis spots of hydrorepellent material, corresponding to about 500 ml of culture were collected from the plate by removing the layer of silica, and extracting the peptides with methanol.

Afterwards the peptides were hydrolyzed in vapour phase in standard hydrolysis tubes and pyrolized at 500° C., according to the procedures reported by Melzer N. M. et al. 1987, Anal. Biochem. 160:356–361. Amino acid analysis was carried out by using the phenyl-thyocarbamil-derivatization method (Cohen S. A. et al. 1988 Anal.Biochem. 174:1–16).

After the hydrolysis reaction the samples were dried to remove HCl completely, neutralized with a 2:1 of methanol/di-isopropilethylamine mixture (20 ml) and then derivatized with a mixture of methanol/di-isopropilethylamine/water/phenylisothyocyanate 7:1:1:1 (20 ml). The reaction mixture was allowed to stand for 10 minutes at room temperature, dried and reconstituted just before injection into a HPLC column for the amino acid analysis. The results obtained are shown in table 1, where the quantities of amino acids are referred to Glu=1.00.

TABLE 1

|  | JH642(pVAL-TE)A | | JH642(pVAL-TE)B | | SURFACTIN | |
| --- | --- | --- | --- | --- | --- | --- |
|  | FOUND | EXPECED | FOUND | EXPECTED | FOUND | EXPECTED |
| GLU | 1.00 | 1.00 | 1.00 | 1.00 | 1.00 | 1.00 |
| VAL | 1.01 | 1.00 | 1.13 | 1.00 | 1.01 | 1.00 |
| LEU | 1.94 | 2.00 | 4.04 | 4.00 | 3.76 | 4.00 |
| ASP | — | — | 0.81 | 1.00 | 1.00 | 1.00 |

These data show that:

1. The fusion of the last 260 amino acids of the srfAORF3 subunit at the end of the fourth activation domain of surfactin synthetase results in the formation of an active peptide synthetase, which synthesizes the lipotetrapeptide with sequence Fatty Acid-Glu-Leu-DLeu-Val which is secreted in quantities comparable to the product of natural surfactin synthetase and 2. the absence of this fusion results in the synthesis of a non-functional peptide synthetase.

We claim:

1. A method for the non-ribosomal production of a peptide of predefined amino acid sequence and length comprising the steps of:
   (a) providing a first DNA sequence containing the coding region of at least one amino acid activating domain of a peptide synthetase;
   (b) providing a second DNA sequence containing the coding region of the carboxy-terminus of the last amino acid binding domain of a peptide synthetase downstream of the amino acid sequence of SEQ ID No. 1;
   (c) fusing the 3'-end of the first DNA sequence to the 5'-end of the second DNA sequence to form a third DNA sequence;
   (d) inserting the third DNA sequence into a vector selected from a group consisting of an expression or an integration vector to form a recombinant vector;
   (e) transforming a microorganism with a recombinant vector of step (d);
   (f) culturing the transformed microorganism to produce the novel peptide synthetase; and
   (g) producing the peptide having a predefined sequence and length using the novel peptide synthetase.

2. The method of claim 1, wherein the vector of step (d) is an integration vector and the novel peptide synthetase is produced by homologous recombination with a first peptide synthetase gene in the microorganism to form a second DNA peptide synthetase gene, wherein the second peptide synthetase encodes a different number of amino acid activating domains than the first peptide synthetase.

3. The method of claim 1, wherein the vector of step (d) is an expression vector and the third DNA sequence encodes a full-length peptide synthetase in which the number and the order of the DDAs is established by the order and number of the amino acids in the peptide to be obtained.

4. The method of claim 1, wherein the step (c) the second DNA sequence is fused to the 3'-end of the first DNA sequence downstream from the region encoding the amino acid sequence of SEQ ID No. 1.

5. The method of claim 4, wherein at least 30 nucleotides are present between the 5'-end of the second DNA sequence and the coding region of the amino acid sequence of SEQ ID No. 1 of the last DDA of the first DNA sequence.

6. The method of claim 1, wherein the last amino acid activating domain of the first DNA sequence comprises a region catalyzing the epimerization of the amino acid.

7. The method of claim 1, wherein the last amino acid activating domain of the first DNA sequence comprises a region catalyzing the methylation of the amino acid.

8. The method of claim 1, wherein the microorganism is selected from the group consisting of a bacterium, a fungus, or a yeast.

9. The method of claim 1, wherein the peptide of predefined sequence and length is produced while the new peptide synthetase is immobilized on a solid insoluble support.

10. The method of claim 1, wherein the peptides of predefined sequence and length have antibiotic, antifungal, immunosuppressive or surfactant properties.

11. A peptide synthetase produced by a method comprising the steps of:
   (a) providing a first DNA sequence containing the coding region of at least one amino acid activating domain of a peptide synthetase;
   (b) providing a second DNA sequence containing the coding region of the carboxy-terminus of the last amino acid binding domain of a peptide synthetase downstream of the amino acid sequence of SEQ ID No. 1;
   (c) fusing the 3'-end of the first DNA sequence to the 5'-end of the second DNA sequence to form a third DNA sequence;
   (d) inserting the third DNA sequence into a vector selected from a group consisting of an expression or an integration vector to form a recombinant vector;
   (e) transforming a microorganism with a recombinant vector of step (d);
   (f) expressing the novel active peptide synthetase by culturing the transformed microorganism of step (e).

12. A peptide synthetase comprising the first four amino acid activation domains of the surfactin synthetase, wherein the fourth amino acid activation domain is fused in the region downstream from the motif encoding the amino acid sequence SEQ ID No. 1 with the carboxy-terminus of the last amino acid binding domain of the surfactin synthetase, wherein the carboxy-terminus region contains at least 260 amino acid residues.

13. The peptide synthetase of claim 12, wherein said peptide synthetase catalyses the production and secretion of an analog of the surfactin having an altered number of amino acids.

* * * * *